United States Patent [19]
Alperin

[11] Patent Number: 5,993,398
[45] Date of Patent: Nov. 30, 1999

[54] METHOD OF MEASURING INTRACRANIAL PRESSURE

[76] Inventor: Noam Alperin, 2853 N. Wolcott, Unit B, Chicago, Ill. 60657

[21] Appl. No.: 09/058,484

[22] Filed: Apr. 10, 1998

[51] Int. Cl.⁶ .................................................. A61B 5/05
[52] U.S. Cl. ......................... 600/561; 600/587; 600/594; 600/595
[58] Field of Search .................................... 600/561, 562, 600/573, 587, 594, 595

[56] References Cited

U.S. PATENT DOCUMENTS

| | | | |
|---|---|---|---|
| 4,204,547 | 5/1980 | Allocca | 600/561 |
| 5,388,583 | 2/1995 | Ragauskas et al. | 128/661.05 |
| 5,617,873 | 4/1997 | Yost et al. | 600/561 |

FOREIGN PATENT DOCUMENTS

WO 95/06435  3/1995  WIPO ............................ A61B 8/04

*Primary Examiner*—Cary O'Connor
*Assistant Examiner*—Pamela L. Wingood
*Attorney, Agent, or Firm*—Welsh & Katz, Ltd.

[57] ABSTRACT

A method and apparatus are provided for measuring intracranial pressure. The method includes the steps of measuring arterial inflow, venous outflow and cranial spinal fluid flow and calculating an intracranial volume change from the measured arterial inflow, venous outflow and cranial spinal fluid flow. The method also includes the steps of calculating a pressure gradient of spinal fluid flow from the measured cranial spinal fluid flow and calculating a pressure change per unit volume change based upon the calculated intracranial volume change and cranial pressure gradient.

24 Claims, 9 Drawing Sheets

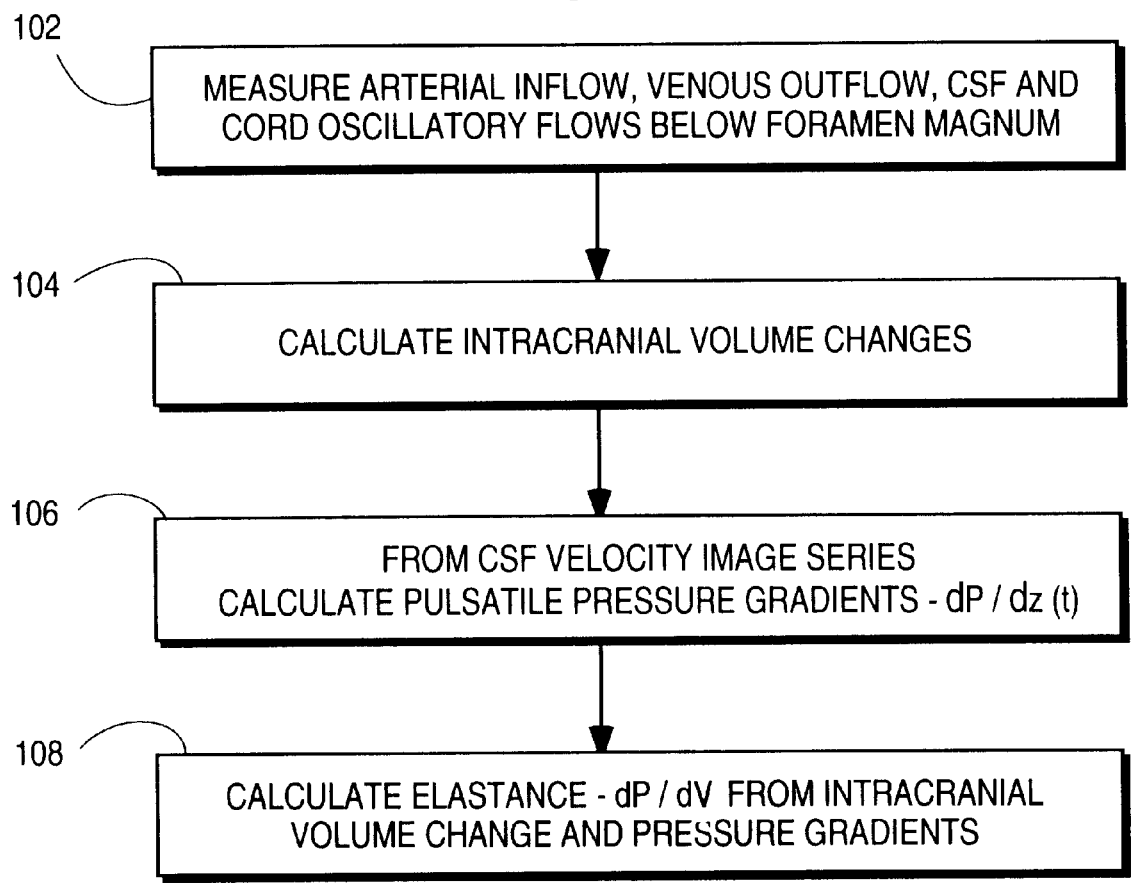

ARTERIAL AND JUGULAR BLOOD VOLUMETRIC FLOW WAVEFORM

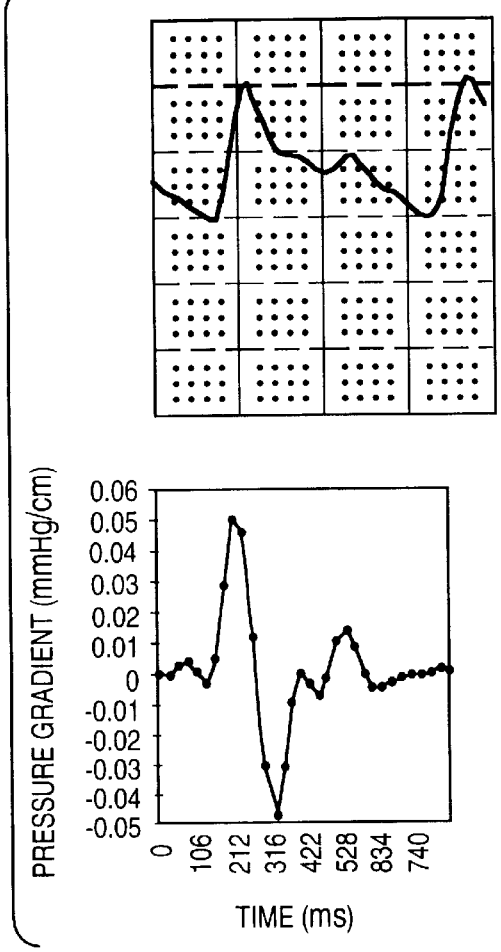
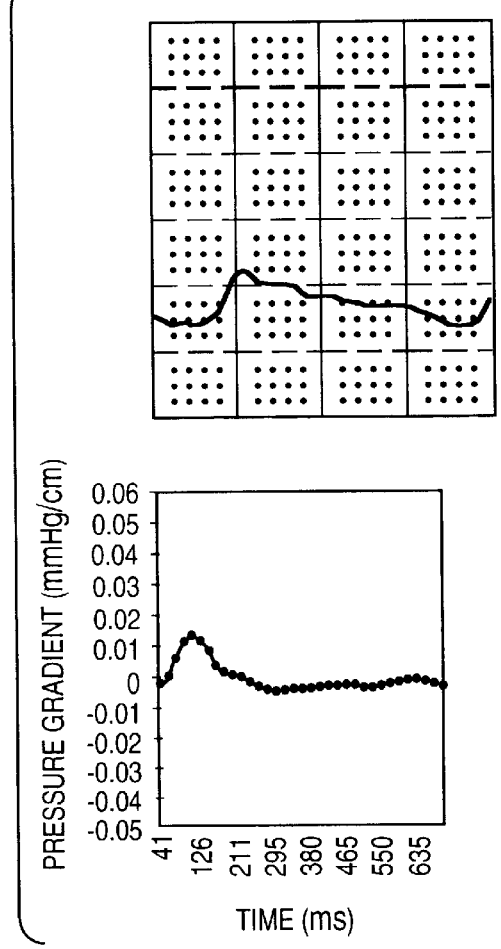
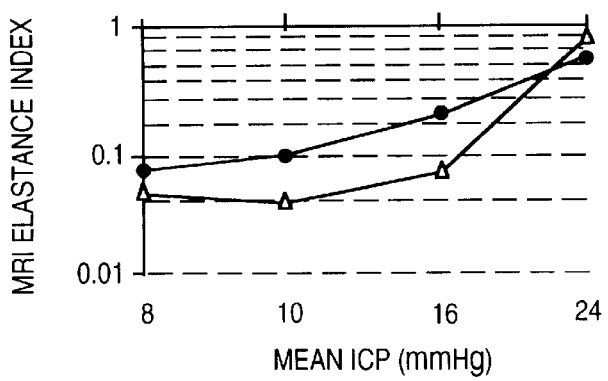

5,993,398

METHOD OF MEASURING INTRACRANIAL PRESSURE

FIELD OF THE INVENTION

The field of the invention relates to medical diagnostic testing and more particularly to methods of measuring intracranial pressure within the cranium of a patient.

BACKGROUND OF THE INVENTION

Intracranial pressure (ICP) and compliance are important clinical parameters for diagnosis and treatment of diseases of the central nervous system (CNS). Elevated intracranial pressure, if left untreated, may result in patient death or permanent damage. Techniques currently available to measure ICP are invasive and associated with risk. In addition, penetration into the CNS space to measure the ICP often alters the pressure.

In a closed system, such as the cranium, the inside pressure and volume are related. The change in pressure due to change in volume is determined by the overall mechanical elastance of the system. Studies of the relation between intracranial volume and pressure date back almost 200 years. In 1873, Alexander Monro stated that the intracranial space contains two compartments (brain matter and blood) that can change in volume. Since neither can be compressed and the cranium is rigid, he concluded that the volume of blood within the intracranial space is constant. Sixty years later, in light of the discovery of the CSF by Magendi, Burrows concluded that intracranial blood volume does change and it is accompanied by a reciprocal change in the volume of the other two compartments, brain and CSF. This is known as the Monro-Kelli doctrine. The majority of the added volume during systole is accommodated by displacement of the CSF into the spinal canal.

Ryder and others injected fluid into the CNS space to find the relation between the intracranial pressure and volume. The derived pressure-volume curve, also called the elastance curve, is well described by a monoexponential curve. The elastance (inverse of compliance) is defined as the change in pressure due to a change in volume (dP/dV). The intracranial elastance (i.e., the derivative of the pressure-volume curve) is therefore also an exponential function of the intracranial volume.

The most practical method of assessing the volume-pressure relationship is the volume pressure test. In this test, the total volume of the system is rapidly loaded by injection of a uniform amount of fluid into the lateral vertical. The pressure change resulting from the volume loading is termed volume-pressure response (VPR).

In both clinical patients and experimental animals, the relationship between VPR and ICP has been shown to be linear. This linear relation validates the monoexponential volume-pressure relation. The elastance coefficient (the coefficient defining the shape of the volume-pressure exponential curve) is determined from the slope of the VPR-ICP linear relationship. The intracranial compliance coefficient is the reciprocal of the elastance coefficient.

In clinical practice, intracranial pressure is often measured for the diagnosis and clinical management of closed-head injuries such as trauma and intracranial bleeding or of chronic disorders such as hydrocephalus, malformations involving hindbrain herniation and pseudotumor cerebri. Intracranial pressure measurement is an invasive procedure and thus it is associated with risk. Accordingly, a need exists for a means of determining ICP using a non-invasive techniques.

BRIEF DESCRIPTION OF THE DRAWINGS

FIG. 4 is a flow chart of the method of the system of FIG. 1;

FIGS. 10a-b depicts further pressure gradient results derived by the apparatus of FIG. 1; and FIG. 11 depicts comparative results of the apparatus of FIG. 1 and invasive intracranial pressure measurements over a wide range of mean ICP in four patients.

APPENDIX I

Appendix I is a source code listing of software that may be used to practice an embodiment of the invention.

SUMMARY

A method and apparatus are provided for measuring intracranial pressure. The method includes the steps of measuring arterial inflow, venous outflow and cranial spinal fluid flow and calculating an intracranial volume change over a cardiac cycle from the measured arterial inflow, venous outflow and cranial spinal fluid flow. The method also includes the steps of calculating over a cardiac cycle a pressure gradient of spinal fluid flow from the measured cranial spinal fluid flow and calculating a pressure change per unit volume change based upon the calculated intracranial volume change and cranial pressure gradient.

DETAILED DESCRIPTION OF A PREFERRED EMBODIMENT

Figure 1:
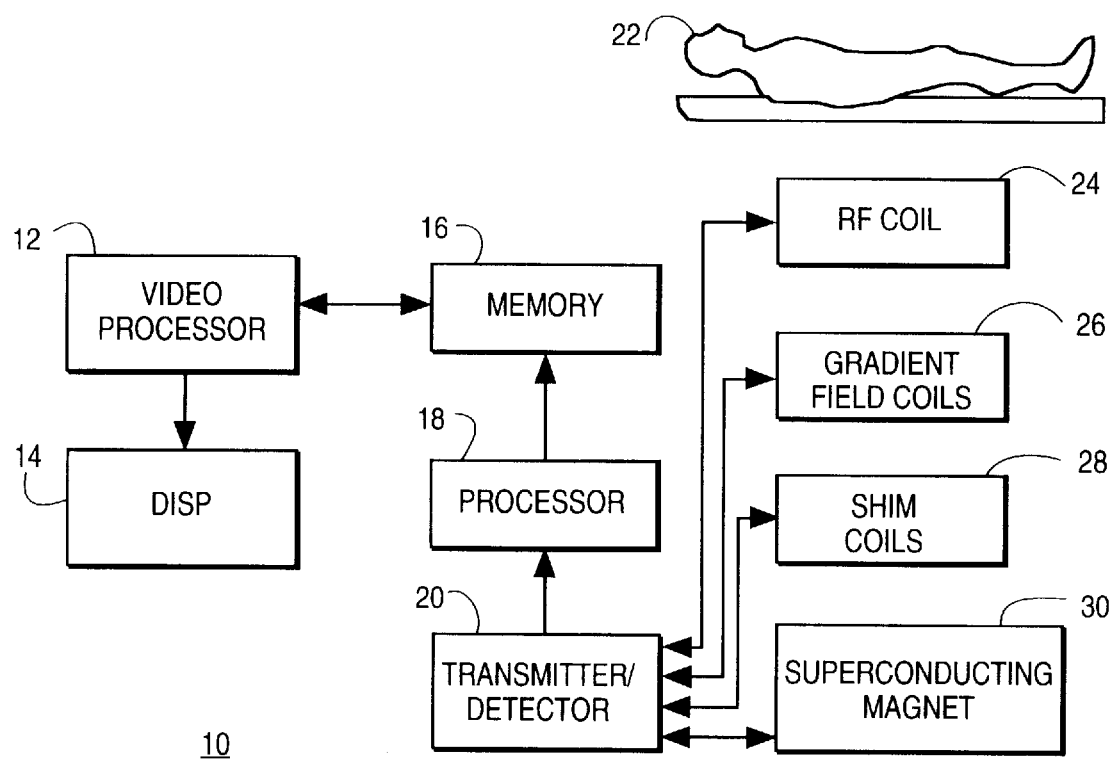
FIG. 1 is a block diagram of apparatus for calculating intracranial pressure in accordance with an embodiment of the invention.

FIG. 1 is a block diagram of a device 10 that may be used to determine intracranial pressure (ICP) non-invasively. Under the embodiment, magnetic resonance imaging (MRI) techniques are used to determine ICP from a series of measurements performed on a subject. The MRI imaging techniques may be used to obtain flow data regarding transcranial (i.e., into and out of the cranium) blood, cranial spinal fluid flow and spinal cord oscillatory movement. The imaging techniques may also be used to obtain data regarding the conduits within which the measured flows occur. Together, the measured values may be used to determine a value of intracranial pressure.

To obtain flow data, an MRI imaging system 10 (e.g., a G.E. Signa 1.5 T) may be set up to measure velocity information at each point (voxel) in three-dimensional space. As is well known in the art, a MRI system 10 may be provided with a superconducting magnet 30, gradient field coils 26 and shim coils 28 to create a varying magnetic field throughout an space (e.g., within the cranium of a patient). The superconducting magnet 30 and gradient field and shim coils 26, 28 provide a varying magnetic field of a known magnitude and variance throughout the measured space. The magnetic field causes atoms (e.g., protons) to align themselves to the magnetic field in a known manner.

A series of radio frequency pulses may be applied to the space at a Larmor frequency of the selected atoms within a selected space. Since the Larmor frequency of the atoms vary as a function of the magnetic field which the atoms experience, only a few atoms at known locations will resonate and generate a measurable signal during a free induction decay (FID) of the electrons of those atoms. A velocity of an atom may be determined by a phase shift of the signal from the selected atoms caused by the movement of the atom within a magnetic field gradient.

By selecting the proper magnetic field and Larmor frequency, a slice of tissue of a subject 22 may be examined in three-dimensional space. Further, since velocity can be determined at any point (area) along the slice of tissue based upon phase shifts, flow through vascular structures (e.g., arteries, veins, etc.) can be determined by integrating and averaging velocity through the selected areas. Determination of flow then becomes the simple step of multiplying velocity times area.

Based upon transcranial fluid flows of a subject, ICP may be determined based upon a set of flow measurement steps, and associated calculations. FIG. 4 is a flow chart 100 which depicts a series of steps that may be used in determining ICP. Reference will be made to FIG. 4 as appropriate to an understanding of the invention.

As a first step 102, flow of blood into and out of the cranium, may be determined. Blood flow into the cranium is pulsatile. Also, at each instant the value of blood flow into the cranium is not equal to blood flow out of the cranium.

However, over the cardiac cycle the integral of blood flow into the cranium is equal to the integral of blood flow out of the cranium except for a very small amount of blood plasma that may be converted into CSF during this cycle. Venous outflow is composed mainly of jugular flow and a small amount of flow that may go through other channels such as the ophthalmic veins. The flow through the other channels is estimated from the constraint that over a caridac cycle inflow equals outflow. The flow through the jugular is measured directly under the process described herein. Not measuring the flow in those other channels doesn't adversely affect ICP results. Stated differently, net arterial inflow does not equal net jugular flow but does equal venous flow that can be calculated from the measured jugular flow.

During each systolic portion of the cardiac cycle, a volume of blood is pumped into the brain through the associated arteries. A delay occurs before an equal amount of blood perfuses through the brain and exits the cranium through the veins. Since blood is incompressible, the differences in volume is, for the most part, accommodated by movement of the cranial spinal fluid and movement of the spinal cord within the spinal column (spinal cord oscillatory flow). The majority of the added volume in the cranium is accommodated in the spinal compartment in the form of displaced CSF, especially at lower levels of increased ICP.

The differences provide a means of determining ICP. To determine ICP, an instantaneous change in the volume of the intracranial content is calculated according to the equation as follows:

$$I(t)=A(t)-V(t)-CSF(t)-Cord(t),$$

where A(t) is the total arterial flow, V(t) is the total venous flow (the sum of the measured jugular flow and the estimated other venous flow), CSF(t) is the rate of CSF outflow through the foramen magnum and Cord(t) is the volumetric rate of spinal cord displacement. More specifically, I(t) can be defined to be the portion of the time-varying arterio-venous flow which is not compensated by the CSF and spinal cord displacement. The integral of I(t) is the time-varying intracranial volume change from which the systolic intracranial volume change may be derived. Time-varying flow rate waveforms may be derived from the MRI phase images by integration of phase values representing the velocities inside regions of interest defining the area of the vessels, the cord and the CSF space.

Figure 5A:
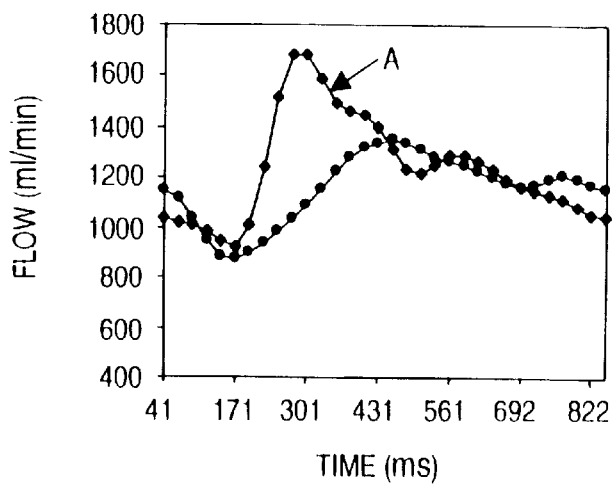
FIGS. 5a-c depicts the time course of arterial and jugular volume flow, CSF and cord flows measured by the apparatus of FIG. 1.
Figure 5B:
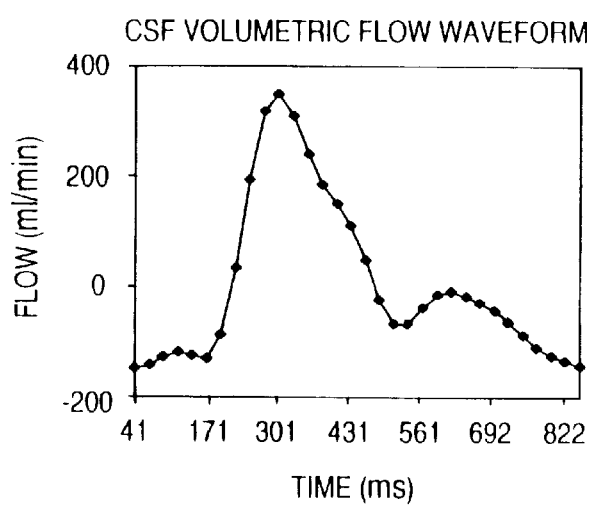
Figure 5C:
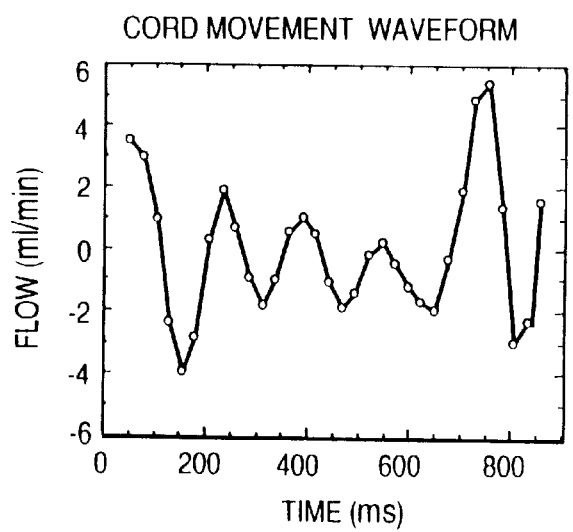

As indicated, the intracranial volume change during the cardiac cycle may be calculated from the time-varying net flow into and out of the cranium. FIGS. 5a–c provides an example of measured data regarding blood flow, cranial spinal fluid flow and cord movement.

Arterial blood inflow and venous outflow may be measured during a first scan using the well-known MRI technique that is optimized for quantification of blood flow. CSF and cord displacement below the foramen magnum may be measured during a second MRI scan that is optimized for slow flow. The two scans are performed in quick succession, at an axial location below the foramen magnum. Blood flow through the four major arteries (two internal carotid and two vertebral) and two veins (jugular) is obtained from one dynamic scan. An example of an MRI phase image representing flow in the major blood vessels is shown in FIG. 2.

Figure 3A:
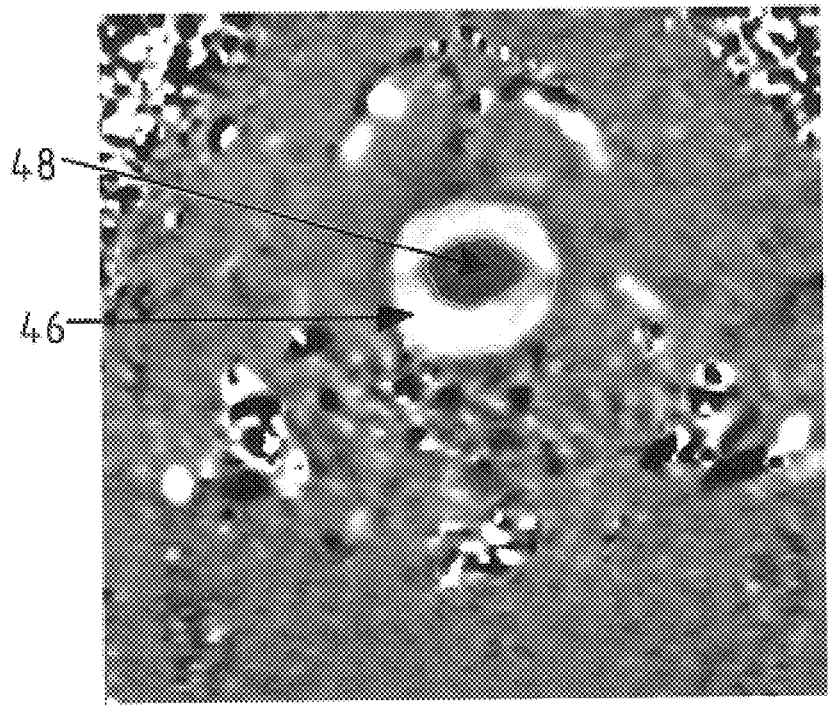
FIGS. 3a-b depicts cranial-spinal fluid and spinal cord images collected by the apparatus of FIG. 1.
Figure 3B:
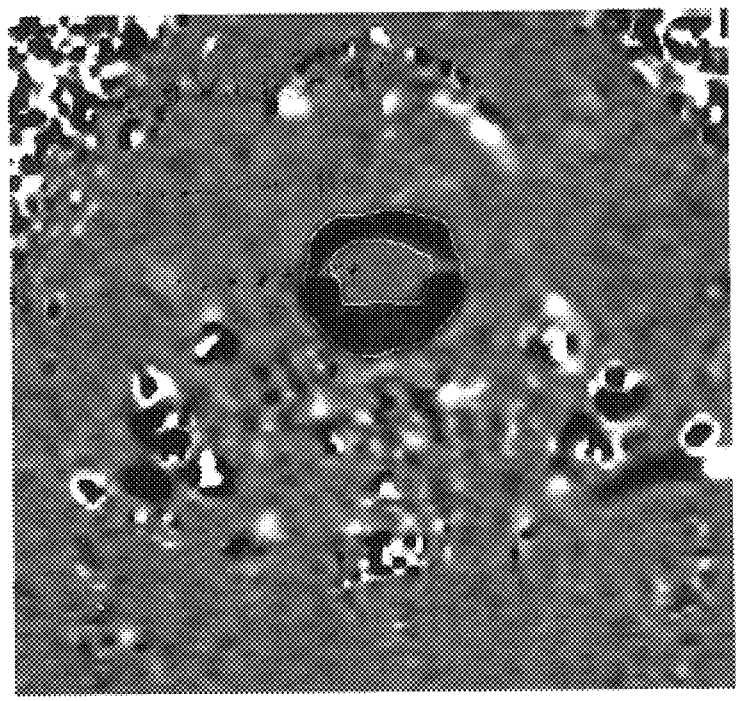

The second scan may be used to measure cervical CSF and cord pulsation. An example of MRI phase images of the CSF flow taken at different cardiac phases are shown in FIGS. 3a-b. In each case, a section 5 mm thick, with a field of view of 1–16 cm, a matrix size of 256×160 mm and two averages may be used. The shortest possible repetition time TR (e.g., 21–26 ms) may be used to optimize temporal resolution (equal to twice the TR). A high velocity encoding (e.g., 80 cm/sec) with flip angle of 20–30 degrees may be used for measurement of blood flow, and a low velocity encoding (e.g., 3–10 cm/sec) with flip angle of 20 degrees may be used for measurements of CSF flow and cord motion. In all scans, the maximum number of time points allowed per cardiac cycle (e.g., 32) may be selected to minimize errors due to interpolation and resampling.

Figure 2:
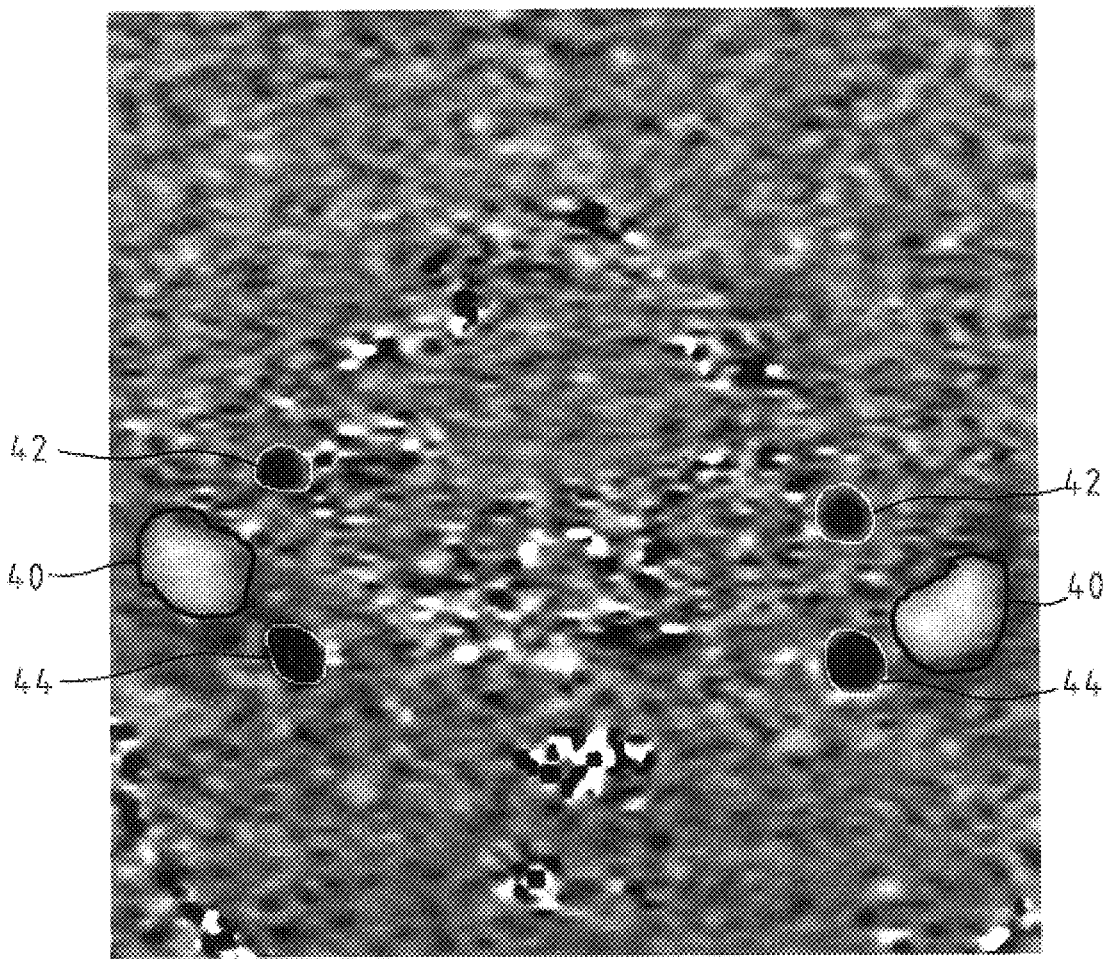
FIG. 2 depicts a blood flow image collected by the apparatus of FIG. 1.

Within FIG. 2 the dark areas 42, 44 depict blood flow into the cranium through the carotid and cerebral arteries. The light areas 40 depicts blood flow out of the cranium through the jugular veins.

To determine a net blood flow, the blood flow within the arteries 42, 44 and veins 40 may each be determined. First the size (e.g., in number of pixels) of each artery and vein may be determined. The number of pixels making up each artery and vein may be determined (marked) by edge-detecting software, or by manually marking the appropriate areas 40, 42, 44 (e.g., by clicking on the appropriate areas with a computer mouse).

Next, a velocity may be determined within each artery and vein. Since the pixel values within the marked areas are a measure of velocity, the velocity values of each pixel within each marked area may be integrated. The integrated velocity may be averaged to determine an average blood flow within the vein or artery.

Finally, the net blood flow may be determined. To determine flow in each vein and artery 40, 42, 44 the average velocities may be multiplied by the areas.

It should be noted, that the determination of net blood flow may be determined in terms of instantaneous values. Each scan may be used to provide a size of each vein and artery, as well as an average velocity and blood flow in that vein or artery for that scan. The result of a series of scans may be a profile of blood flow for each vein and artery during each point of the cardiac cycle.

FIGS. 3a-b shows a phase contrast image of CSF pulsatile flow. The light area 46 in the center of FIG. 3a shows the outward flow of cranial spinal fluid during systole. The corresponding dark area of FIG. 3b shows the inward flow of CSF during diastole. The area 48 in the center of the CSF 46 depicts the spinal cord.

It has been found that in addition to blood and CSF flow, that spinal cord movement may also be considered in net flow considerations. However, it can be seen from a comparison of the flows of FIGS. 5a–c that ignoring spinal cord movement may not result in significant error.

Flow of the CSF and spinal cord may be determined as part of a two step process. First the spinal cord 48 is marked as described above and a spinal cord oscillatory flow is determined as discussed above. Since the cross-sectional area of the cord moves as a unit, one or two pixel values may be sufficient to determine velocity. Under a preferred embodiment all pixels within the cord area are integrated (summed) to obtain an average cord velocity.

Next, a flow in the annular area of the CSF between lines 46 and 48 may be determined. An outer periphery 46 (i.e., the dura) of the CSF is marked. The pixels of the spinal cord 48 is excluded from area and velocity determinations of the CSF. As above, the area of the annular area is determined and a CSF flow may be determined from an average velocity.

Since the flow is in an annular area, the measurement of velocity is somewhat more complicated. To insure an accurate average of velocity, flow across the annulus may be determined by integrating a velocity of each pixel around the annulus.

With a knowledge of flows into and out of the cranial space of a the subject, the value I(t) may be determined. From I(t), a value for ICP may be determined once a cranial pressure gradient (dP/dz) has been calculated.

To determine dP/dz, the area below the foramen magnum is again considered. For example, where CSF and spinal cord oscillatory flow are considered within a confined space (e.g., mid C2 region), the value for dP/dz can be calculated or determined with a high degree of accuracy, using convention pressure-flow equations.

A determination of dp/dZ has not been widely used in the past in arteries or veins because of the elastic periphery of such conduits. Within the C2 vertebra, the dura of the CSF is attached to the surrounding bone and provides a rigid tube which facilitates accurate measurements.

Under a preferred embodiment, dP/dz may be calculated for the CSF using the Navier-Stokes equation or Womersley Pressure-Flow Relation within the annular area containing the CSF. Such calculations may be accurately based upon assumptions including: no in-plane velocities, rigid walls of the space and minimum curvature along an axis of the conduit.

Within the annular area bounding the CSF, the space between the spinal cord and dura bounding the CSF may be relatively precisely determined. A velocity across that determined space may also be determined (or may also have been determined during flow measurements). The pressure gradient waveform may be calculated using the Navier-Stokes equation. The Navier-Stokes equation includes two terms inertial and viscous loss.

$$-\rho(\delta v/\delta t + v \cdot \nabla v) + \mu \nabla^2 v = \nabla p$$

The inertial component of the pressure gradient is approximated by the first order central difference template of the time series images and the shear component is derived by using a piar of second order central difference operators. The sum of the shear and inertia components in the region of interest which includes only the CSF pixels where added to derive mean pressure for each phase of the cardiac cycle.

When Womersley pressure flow relationships are used, the CSF flow and its time derivative are used to derive the pressure gradient waveforms.

$$\partial P/\partial z = I(\partial Q/\partial t) + RQ$$

Figure 6A:
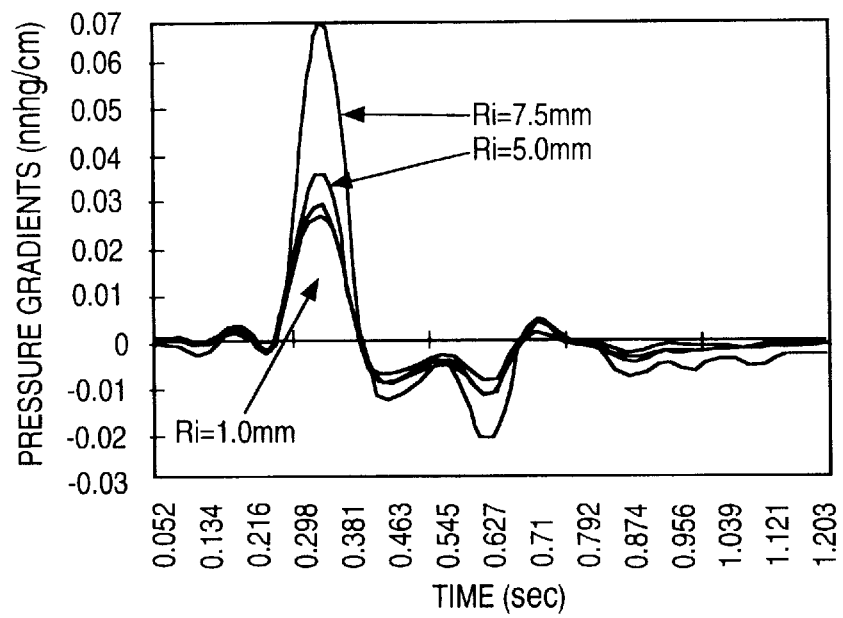
FIGS. 6a-b depicts pressure gradient calculations of the apparatus of FIG. 1.
Figure 6B:
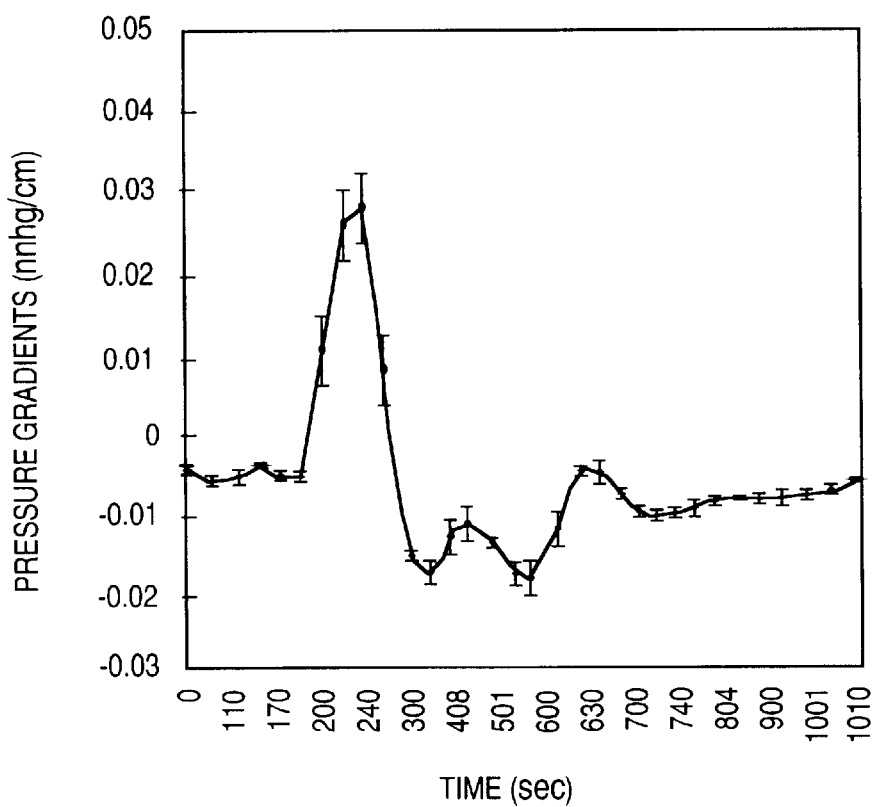

FIG. 6a provides a profile of pressure gradient versus time using the Womersley Pressure Flow Relationship. FIG. 6a shows pressure gradient waveforms derived from flow information for 4 different circular annulus cross-sectional areas. FIG. 6b is a gradient waveform derived using CSF velocity images and the Navier-Stokes equation.

As may be noted from FIG. 6a, the pressure gradient is highly dependent upon the size of the annulus. For example, the diameter of the CSF 46 for purposes of FIG. 6a was assumed to be 10.0 mm. To obtain a final value from the Womersley Pressure Flow Relationship the pressure gradient must be multiplied by an area of the annulus.

The concentric annulus model of FIG. 6a was used to evaluate the effect of the CSF cross-sectional area on the derived pressure gradient waveforms. Pressure gradient waveforms were derived for 4 models of concentric circular annulus with outer radius of 10 mm and inner radius that varied from 1 mm to 7.5 mm. The same CSF flow waveform was used for the 4 models. The derived waveforms are shown in FIG. 6a. The derived waveforms had similar shape but were different by a scale factor. This result suggests that normalization of the pressure gradients with the CSF cross-sectional area provides a way to obtain pressure gradients that are not velocity dependent, but are flow dependent. As a result, it is possible to compare pressure gradients derived form spinal canals that may differ in the CSF cross-sectional area.

FIG. 6b provides a pressure gradient derived from the velocity images and the Navier-Stokes equation.

Figure 9:
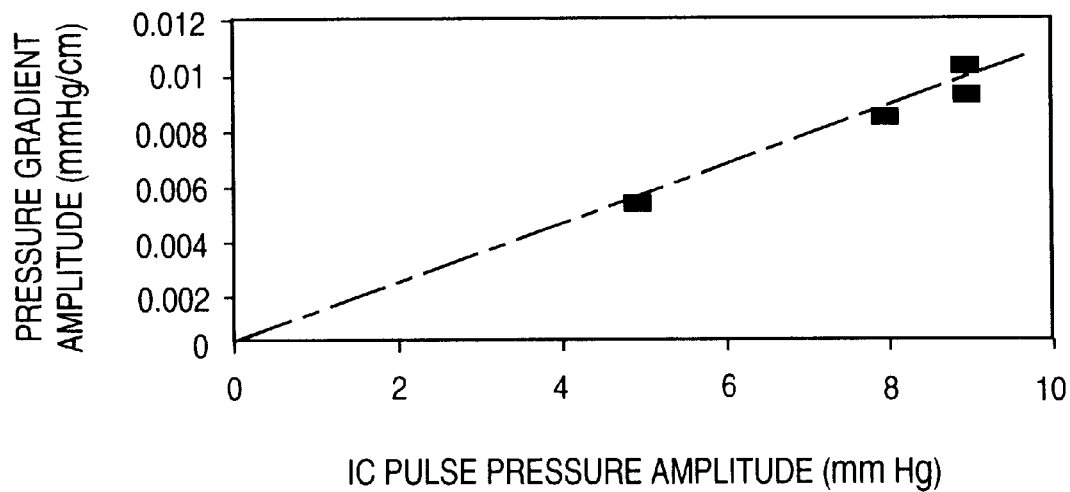
FIG. 9 depicts pressure gradient amplitude measured by the apparatus of FIG. 1.

FIG. 9 shows experimental results from a baboon comparing amlitude of MRI derived pulse pressure gradient and amplitude of invasively measured ICP pulse pressure at three different values of mean intracranial pressures. The relations obtained in this experiment are used when pulse pressure is estimated from MRI pressure gradients.

Figure 7:
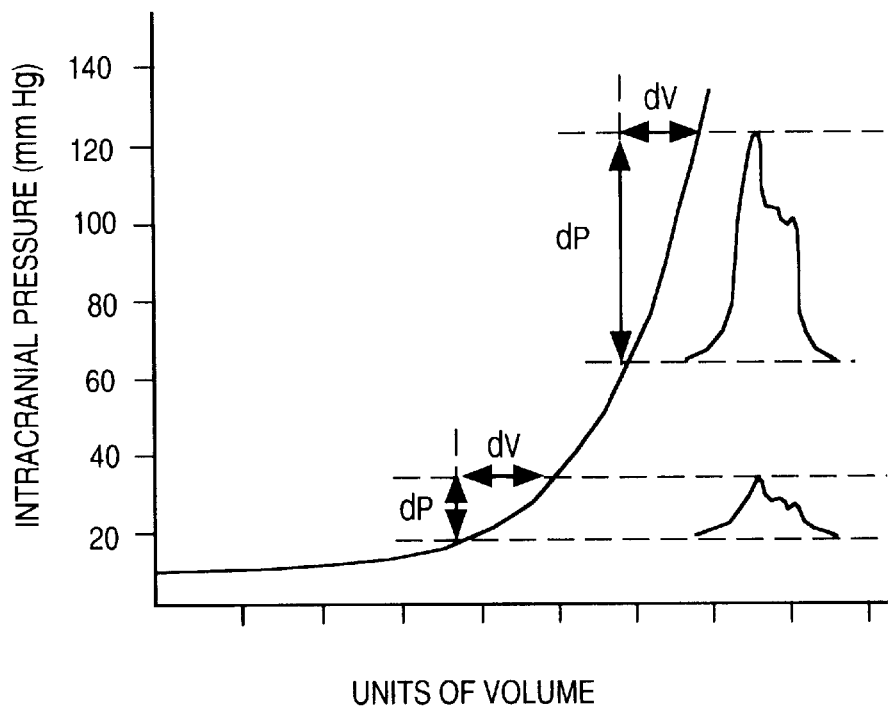
FIG. 7 depicts the elastance curve used by the apparatus of FIG. 1.
Figure 8:
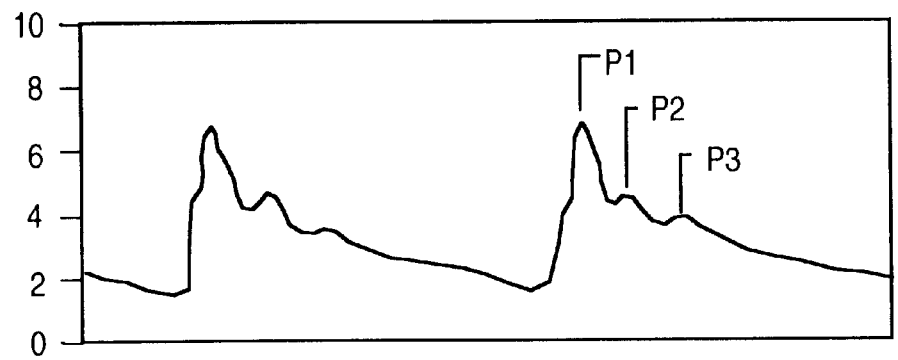
FIG. 8 depicts invasive recording of intracranial pressure forms causing the flows measured by the apparatus of FIG. 1.

FIG. 7 describes the ICP volume relationship which is described by the following expression:

$$P = P_1 \exp\{a(V - V_{eq})\} + P_o,$$

which is a monoexponential curve also known as the elastance curve. The derivative of this curve is therefore also an expontial curve therefore the following relationship exists between ICP and elastance:

$$dP/dV = a\{P - P_o\} = ac\{ICP\}.$$

DP/dv is estimated from the MRI derived pressure gradients and amplitude of the of the intracranial volume change. This value also referred to as elastance index is related to the ICP as expressed by the derivative of the elastance curve. The elastance curve is shown in FIG. 7. A relationship exists between the elastance index and intracranial pressure. (As is shown in FIG. 11).

FIG. 11 shows the relationship between the MRI derived elastance index and mean ICP. In specific, FIG. 10 shows the correlation between MRI derived elastance indexes and ICP for four patients (circles indicate data normalized for CSF area). As should be noted (neglecting the logarithmic scale) a linear relationship exists between elastance and ICP.

FIGS. 10a-b shows comparative data between pressure gradient and ICP. FIG. 11a shows a pressure gradient of a patient with a low ICP within a normal range. FIG. 11b shows a pressure gradient profile for a patient with an elevated ICP.

Table I shows comparative data from baboon experimentation. As shown, the MRI-derived data shows extremely good correlation to the invasively derived data.

TABLE I

| | Invasive | | MRI-Derived | | | |
|---|---|---|---|---|---|---|
| | HR (bpm) | Mean ICP (mmHg) | HR (MRI) (bpm) | PTP Pr Grd (mm/Hg/cm) | PTP Vol. Change | Elastance dP/dV |
| Rest | 80 | 12 | 80 | 0.029 | 0.17 | 0.16 |
| High | 82 | 24 | 81 | 0.023 | 0.09 | 0.26 |
| Low | 84 | 9 | 86 | 0.016 | 0.17 | 0.093 |

Table II shows comparative data for four patents. As with the baboon data, the MRI derived data shows extemely good correlation with the invasively derived data.

TABLE II

| | HR (ICU) (bpm) | Mean ICP (mmHg) | PTP ICP (mmHg) | HR (MRI) (bpm) | PTP Pr Grad (mm/Hg/cm) (A) | CSF flow area (cm$^2$) (C) | PTP Vol Chng (cc) (B) | Elast. dP/dV = (A/B) | Elast. Norm. for CSF ar = (A/B) × C |
|---|---|---|---|---|---|---|---|---|---|
| Pt. #1 | 69 | 10 | 3.75 | 81 | 0.016 | 2.43 | 0.44 | 0.036 | 0.087 |
| Pt. #2 | 100 | 8 | 3.0 | 94 | 0.018 | 1.36 | 0.36 | 0.049 | 0.067 |
| Pt. #3 | 110 | 16 | 6.75 | 75 | 0.098 | 2.91 | 1.38 | 0.071 | 0.207 |
| Pt. #4* | — | 24 | — | 82 | 0.062 | 0.60 | 0.073 | 0.845 | 0.547 |

* = invasive ICP measured with lumbar punature.

A preliminary comparison of invasive pressure measurements and MRI-derived measurements were obtained A preliminary comparison of invasive pressure measurements and MRI-derived measurements were obtained from two baboon studies (the second study is shown in Table I) and from four patients who were monitored for ICP at the time of the MRI study (Table II). A summary of the results and their importance to this project are described below.

In the first experiment, mean ICP was controlled by changing the fluid volume in the CNS (i.e., the transcranial blood flow was unchanged). Under these conditions, a linear relationship may be found between the peak to peak (PTP) amplitude of the MRI-derived CSF pulsatile pressure gradient and the PTP amplitude of the ICP. The results are shown in FIG. 9. A similar correlation was found between the PTP amplitude of the MRI-derived pressure gradients and the means ICP.

The experiment was repeated. This time the mean ICP was modified by restricting the jugular venous outflow (Valsalva maneuver). In this experiment, the hemodynamic state is different at each level of the mean ICP. As expected, there was no correlation between the PTP amplitude of the MRI-derived pressure gradients and the mean ICP. However, it would be expected to find a correlation between MRI-derived elastance (dV/dP) and means ICP.

The elastance index can be estimated from the ratio of the PTP amplitude of the MRI-derived pressure gradients and the PTP amplitude of intracranial volume change. The results of the second experiment are summarized in Table I. As expected, when hemodynamic changes occurs in conjunction with change in the mean ICP, the elastance, and not the PTP pressure gradients, is correlated with the mean ICP value.

Pressure measurements were also obtained from four patients who underwent an MRI study (Table II) and were monitored for ICP with a short external ventricular drainage catheter (EVD) which was inserted into their lateral ventricle. The measured and derived parameters from the patients are summarized in Table II.

Patient 1 and 2 had mean ICP values within the normal range, while patient 3 had an elevated mean ICP, and patient 4 had extremely elevated ICP. The ICP measurements covers a large portion of the practical range expected for ICP measurements. Though the MRI measurements and the ICP recordings were not measured simultaneously (measurements were made from an hour to several hours apart), there was good correspondence between mean ICP, measured invasively, and the MRI-derived estimate for the elastance. It is clear that using the CSF flow area for normalization of the PTP pressure gradients improves the correspondence between the elastance and the mean ICP. Actual ICP recordings and the corresponding MRI-derived pressure gradients are shown in FIGS. 11a and 11b, respectively. These results indicate that the sensitivity of the MRI measurements are within the range needed to differentiate between normal and elevated ICP.

A specific embodiment of a novel method and apparatus for determining intracranial pressure according to the present invention has been described for the purpose of illustrating the manner in which the invention is made and used. It should be understood that the implementation of other variations and modifications of the invention and its various aspects will be apparent to one skilled in the art, and that the invention is not limited by the specific embodiments described. Therefore, it is contemplated to cover the present invention any and all modifications, variations, or equivalents that fall within the true spirit and scope of the basic underlying principles disclosed and claimed herein.

I claim:

1. A method of measuring intracranial pressure comprising the steps of:

measuring arterial inflow, venous outflow and cranial spinal fluid flow;

calculating an intracranial volume change over a cardiac cycle from the measured arterial inflow, venous outflow and cranial spinal fluid flow;

calculating a pressure gradient over a cardiac cycle of spinal fluid flow from the measured cranial spinal fluid flow; and calculating a pressure change per unit volume change based upon the calculated intracranial volume change and cranial pressure gradient.

2. The method of measuring intracranial pressure as in claim 1 wherein the step of measuring further comprises measuring spinal cord movement.

3. The method of measuring intracranial pressure as in claim 2 wherein the step of measuring a cranial spinal fluid flow and spinal cord movement further comprises determining a cross-sectional area of the spinal cord and an annular area between the spinal cord and a dura matter of the spinal cord.

4. The method of measuring intracranial pressure as in claim 3 wherein the step of measuring the area of the spinal cord and annular area further comprises forming a magnetic resonance image and integrating an area of the spinal cord and the annular area between the spinal cord and dura matter.

5. The method of measuring intracranial pressure as in claim 4 wherein the step of measuring a cranial spinal fluid flow and spinal cord oscillatory flow further comprises measuring a velocity of the cranial spinal fluid flow velocity across the annular area between the spinal cord and the dura matter and a velocity of the spinal cord.

6. The method of measuring intracranial pressure as in claim 5 wherein the step of measuring cranial spinal fluid flow and spinal cord oscillatory flow further comprises forming a magnetic resonance image and determining a velocity of the cranial spinal fluid flow within the annular space.

7. The method of measuring intracranial pressure as in claim 6 wherein the step of calculating a pressure gradient of spinal fluid flow further comprises calculating a pressure gradient using the Navier-Stokes equation based upon the determined size of the annular area and determined velocity of the cranial spinal fluid flow.

8. The method of measuring intracranial pressure as in claim 6 wherein the step of measuring a cranial pressure gradient further comprises calculating a pressure gradient using the Womersley Pressure-Flow Relation based upon the determined annular size and determined velocity of the cranial spinal fluid flow.

9. The method of measuring intracranial pressure as in claim 1 wherein the step of measuring arterial inflow and venous outflow further comprises determining a cross-sectional area of two carotid and two vertebral arteries and two jugular veins.

10. The method of measuring intracranial pressure as in claim 9 wherein the step of measuring a cross-sectional area further comprises forming a magnetic resonance image and integrating an area within two carotid and two vertebral arteries and two jugular veins.

11. The method of measuring intracranial pressure as in claim 10 wherein the step of measuring arterial inflow and venous outflow further comprises determining a velocity of blood flow in two carotid and two vertebral arteries and two jugular veins.

12. The method of measuring intracranial pressure as in claim 11 wherein the step of measuring arterial inflow and venous outflow further comprises forming a magnetic resonance image and determining blood velocity within two carotid and two vertebral arteries and two jugular veins.

13. Apparatus for measuring intracranial pressure comprising:
means for measuring arterial inflow, venous outflow and cranial spinal fluid flow;
means for calculating an intracranial volume change over a cardiac cycle from the measured arterial inflow, venous outflow and cranial spinal fluid flow;
means for calculating a pressure gradient over a cardiac cycle of spinal fluid flow from the measured cranial spinal fluid flow; and
means for calculating a pressure change per unit volume change based upon the calculated intracranial volume change and cranial pressure gradient.

14. The apparatus for measuring intracranial pressure as in claim 13 further comprising means for calculating spinal cord movement.

15. The apparatus for measuring intracranial pressure as in claim 14 wherein the means for measuring a cranial spinal fluid flow and spinal cord movement flow further comprises means for determining a cross-sectional size of the spinal cord and an annular area between the spinal cord and a dura matter of the spinal cord.

16. The apparatus for measuring intracranial pressure as in claim 15 wherein the means for measuring the size of the spinal cord and annular area further comprises means for forming a magnetic resonance image and integrating an area of the spinal cord and the annular area between the spinal cord and dura matter.

17. The apparatus for measuring intracranial pressure as in claim 16 wherein the means for measuring a cranial spinal fluid flow and spinal cord oscillatory flow further comprises means for measuring a velocity of the cranial spinal fluid flow velocity across the annular area between the spinal cord and the dura matter and a velocity of the spinal cord.

18. The apparatus for measuring intracranial pressure as in claim 17 wherein the means for measuring cranial spinal fluid flow and spinal cord oscillatory flow further comprises means for forming a magnetic resonance image and determining a velocity of the cranial spinal fluid flow within the annular space.

19. The apparatus for measuring intracranial pressure as in claim 18 wherein the means for calculating a pressure gradient of spinal fluid flow further comprises means for calculating a pressure gradient using the Navier-Stokes equation based upon the determined size of the annular area and determined velocity of the cranial spinal fluid flow.

20. The apparatus for measuring intracranial pressure as in claim 19 wherein the means for measuring a cranial pressure gradient further comprises means for calculating a pressure gradient using the Womersley Pressure-Flow Relation based upon the determined annular size and determined velocity of the cranial spinal fluid flow.

21. The apparatus for measuring intracranial pressure as in claim 14 wherein the means for measuring arterial inflow and venous outflow further comprises means for determining a cross-sectional area of two carotid and two vertebral arteries and two jugular veins.

22. The apparatus for measuring intracranial pressure as in claim 21 wherein the means for measuring a cross-sectional area further comprises means for forming a magnetic resonance image and integrating an area within two carotid and two vertebral arteries and two jugular veins.

23. The apparatus for measuring intracranial pressure as in claim 22 wherein the means for measuring arterial inflow and venous outflow further comprises means for determining a velocity of blood flow in two carotid and two vertebral arteries and two jugular veins.

24. The apparatus for measuring intracranial pressure as in claim 23 wherein the means for measuring arterial inflow and venous outflow further comprises means for forming a magnetic resonance image and determining blood velocity within two carotid and two vertebral arteries and two jugular veins.

* * * * *